United States Patent [19]
Alfano et al.

[11] Patent Number: 5,769,081
[45] Date of Patent: Jun. 23, 1998

[54] METHOD FOR DETECTING CANCEROUS TISSUE USING OPTICAL SPECTROSCOPY AND FOURIER ANALYSIS

[75] Inventors: Robert R. Alfano; Alvin Katz, both of Bronx; Yuanlong Yang, New York, all of N.Y.

[73] Assignee: The Research Foundation of City College of New York, New York, N.Y.

[21] Appl. No.: 618,459

[22] Filed: Mar. 18, 1996

[51] Int. Cl.$^6$ ....................................................... A61B 6/00
[52] U.S. Cl. ............................ 128/665; 356/301; 356/318
[58] Field of Search .................................. 128/665, 664, 128/633, 634; 356/301, 317–320

[56] References Cited

U.S. PATENT DOCUMENTS

| 4,930,516 | 6/1990 | Alfano et al. . |
|---|---|---|
| 5,369,496 | 11/1994 | Alfano et al. . |

OTHER PUBLICATIONS

Francheschi et al., "In Vivo Fast Fourier Transform Analysis of the Autofluorescence of Normal and Neoplastic Upper Aerodigestive Mucosa" Surgical Oncology, vol. XLV, pp. 488–492 (1994).

Tang et al., "Native fluorescence spectroscopic detection of the effects of chemotherapeutic retinoids on a cancer model of the aerodigestive tract," Optics for protection of man and envir. against natural and technological diasasters, G. von Bally and H.I. Bjelkhagen editors, Elsevier Science Publisher (1993).

Glassman et al., "Ultraviolet Excited Fluorescence Spectra from Non–malignant and Malignant Tissues of the Gynecological Tract," Lasers in the Life Sciences, 5(1–2):49–58 (1992).

Yang et al., "Fluorescence Spectroscopy as a Photonic Pathology Method for Detecting Colon Cancer," Laser in the Life Sciences, 6(4):259–76 (1995).

Richards–Kortum et al., "Spectr. Diagnosis of Colonic Dysplasia," Photochemistry and Photobiology, 53(6):777–86 (1991).

Schomacker et al., "Ultraviolet Laser–Induced Fluorescence of Colonic Tissue: Basic Biology and Diagnostic Potential," Lasers in Surgery and Medicine, 12:63–78 (1992).

Alfano et al., "Light Sheds Light on Cancer–Distringuishing Malignant Tumors from Benign Tissues and Tumors," the Bulletin of the New York Academy of Medicine, 67(2):143–50 (1991).

Tang et al., "Spectr. Diff. between Human Cancer and Normal Lung and Breast Tissues," Lasers in Surgery and Medicine, 9:290–5 (1989).

Alfano et al., "Fluorescence Spectra from Cancerous and Normal Homan Breast and Lung Tissues," IEEE J. Quantum Electron., vol. QE–23, No. 10, 1806–11 (1987).

Alfano et al., "Laser Induced Fluorescence Spectroscopy from Native Cancerous and Normal Tissue," IEEE J. Quantum Electron., vol. QE–20, No. 12, 1507–16 (1984).

*Primary Examiner*—Ruth S. Smith
*Attorney, Agent, or Firm*—Kriegsman & Kriegsman

[57] ABSTRACT

A method for detecting cancerous tissue using optical spectroscopy and Fourier analysis. According to a preferred embodiment, a tissue sample is illuminated with light at a wavelength of approximately 300 nm. Next, a fluorescence emission spectrum for the tissue sample is obtained by measuring the resultant fluorescence from the tissue sample over the spectral region from approximately 320 nm to approximately 580 nm. The phase and amplitude for the first three Fourier transform harmonics are then determined. The phase and amplitude determinations for one or more of the three harmonics are then compared to appropriate standards obtained from cancerous and non-cancerous tissue samples. The accuracy of the method can be improved further by comparing the phase and amplitude calculations for at least two harmonics.

30 Claims, 10 Drawing Sheets

METHOD FOR DETECTING CANCEROUS TISSUE USING OPTICAL SPECTROSCOPY AND FOURIER ANALYSIS

BACKGROUND OF THE INVENTION

The present invention relates generally to methods for detecting cancer using optical spectroscopy and more particularly to a new and improved method for detecting cancer using optical spectroscopy.

Because a sufficiently effective method for preventing cancer has not yet been discovered, cancer research has focused on the most effective ways of treating cancer. As different as the various forms of treatment have been—ranging from excision to radiation to chemotherapy—all treatments have relied on one crucial step, the detection of cancerous tissue. The importance of detection cannot be stressed enough. Early detection not only indicates the presence and location of cancer but also may indicate where cancer originated and what types of treatment will be most safe and effective. In addition to being used to detect cancer as early as possible, detection methods may also serve as a means of monitoring the efficacy of treatment methods.

Traditionally, cancer detection methods have relied on imaging techniques involving the use of X-rays, nuclear magnetic resonance or nuclear radiation or have relied on invasive methods involving biopsy and chemical laboratory analysis.

Over the past several years, however, considerable research has been conducted on the use of optical spectroscopy as a means of cancer detection. Optical spectroscopy (defined herein as including, but not being limited to, fluorescence spectroscopy (excitation, emission or time-resolved), Raman spectroscopy, absorption spectroscopy and diffuse reflective spectroscopy) holds promise as a source for a wide-range of diagnostic tools for in vivo and in vitro cancer detection. Examples of techniques using optical spectroscopy in cancer detection are set forth below.

In U.S. Pat. No. 5,413,108, inventor Alfano, which issued May 9, 1995 and which is incorporated herein by reference, there are disclosed a method and an apparatus for examining a two-dimensional region of a tissue sample. This is accomplished, according to one embodiment of the invention, by illuminating, i.e., exciting, the two-dimensional tissue sample with light at a first wavelength. The resultant fluorescence is then measured at an emission wavelength as a function of location within the two-dimensional tissue sample. The two-dimensional tissue sample is then illuminated again with light at a second wavelength, and the resultant fluorescence is measured at the same emission wavelength. The two excitation wavelengths and the emission wavelength are appropriately chosen so that the ratio or difference of fluorescence intensities at the emission wavelength is indicative of the carcinomatous condition of the tissue. A value, such as a ratio or difference, of the respective intensity measurements obtained at each location of the tissue sample is then calculated. These values are then compared to appropriate standards, and the results are depicted in the form of a map. The invention is premised on the discovery that certain native, commonly-occurring molecules, such as collagen, NAD$^+$/NADH, NADP$^+$/NADPH, flavins, tryptophan, and elastin, fluoresce differently in cancerous tissue than in non-cancerous tissue.

In U.S. Pat. No. 5,348,018, inventors Alfano et al., which issued Sep. 20, 1994 and which is incorporated herein by reference, there is disclosed a method for determining if tissue is malignant as opposed to non-malignant (i.e., benign tumor tissue, benign tissue, or normal tissue). In one embodiment, the method comprises irradiating a human breast tissue sample with light at a wavelength of about 310 nm and measuring the time-resolved fluorescence emitted therefrom at about 340 nm. The time-resolved fluorescence profile is then compared to similar profiles obtained from known malignant and non-malignant human breast tissues. By fitting the profiles to the formula $I(t)=A_1 e(-t/\tau_1)+A_2 e(-t/\tau_2)$, one can quantify the differences between tissues of various conditions. For example, non-malignant human breast tissues exhibit a slow component ($\tau_2$) which is less than 1.6 ns whereas malignant human breast tissues exhibit a slow component ($\tau_2$) which is greater than 1.6 ns. In addition, non-malignant human breast tissues exhibit a ratio of fast to slow amplitudes ($A_1/A_2$) which is greater than 0.85 whereas malignant human breast tissues exhibit a ratio of fast to slow amplitudes ($A_1/A_2$) which is less than 0.6. This technique can be used with different excitation and/or emission wavelengths, and can be applied to the detection of malignancies (or other abnormal states) in tissues other than human breast tissue.

In U.S. Pat. No. 5,261,410, inventors Alfano et al., which issued Nov. 16, 1993 and which is incorporated herein by reference, there is disclosed a method for determining if a tissue is a malignant tumor tissue, a benign tumor tissue, or a normal or benign tissue. The present method is based on the discovery that, when irradiated with a beam of infrared, monochromatic light, malignant tumor tissue, benign tumor tissue, and normal or benign tissue produce distinguishable Raman spectra. For human breast tissue, some salient differences in the respective Raman spectra are the presence of four Raman bands at a Raman shift of about 1078, 1300, 1445, and 1651 cm$^{-1}$ for normal or benign tissue, the presence of three Raman bands at a Raman shift of about 1240, 1445, and 1659 cm$^{-1}$ for benign tumor tissue, and the presence of two Raman bands at a Raman shift of about 1445 and 1651 cm$^{-1}$ for malignant tumor tissue. In addition, it was discovered that for human breast tissue the ratio of intensities of the Raman bands at a Raman shift of about 1445 and 1659 cm$^{-1}$ is about 1.25 for normal or benign tissue, about 0.93 for benign tumor tissue, and about 0.87 for malignant tumor tissue.

In U.S. Pat. No. 5,131,398, inventors Alfano et al., which issued Jul. 21, 1992 and which is incorporated herein by reference, there are disclosed a method and an apparatus for distinguishing cancerous tumors and tissue from benign tumors and tissue or normal tissue using native fluorescence. The tissue to be examined is excited with a beam of monochromatic light at 300 nanometers (nm). The intensity of the native fluorescence emitted from the tissue is measured at 340 and 440 nm. The ratio of the two intensities is then calculated and used as a basis for determining if the tissue is cancerous as opposed to benign or normal. The invention is based on the discovery that when tissue is excited with monochromatic light at 300 nm, the native fluorescence spectrum over the region from about 320 nm to 600 nm is different for tissue that is cancerous than for tissue that is benign or normal. The technique is useful in either in vivo or in vitro testing of human as well as animal tissue.

In U.S. Pat. No. 4,930,516, inventors Alfano et al., which issued June 5, 1990 and which is incorporated herein by reference, there are disclosed a method and an apparatus for detecting the presence of cancerous tissue using visible luminescence. The tissue to be examined is excited with a beam of monochromatic light that causes the tissue to fluoresce over a spectrum of wavelengths. The intensity at which the excited tissue fluoresces can be measured either over a spectrum or at a predetermined number of preselected wavelengths. By determining the wavelength(s) at which maximum intensity(ies) are attained for the tissue in question and by comparing these peak wavelengths, either visually or electronically, to the peak wavelength(s) derived from a known non-cancerous tissue, or by comparing the spectrum of the excited tissue with the spectrum of a known noncancerous tissue one can determine the carcinomatoid status of the tissue in question. The invention is based on the discovery that the visible luminescence spectra for cancerous and non-cancerous tissue are substantially different and that the differences are such that visible luminescence from tissue can be used to detect the presence of cancer.

Other patents and publications of interest include, Franceschi et al., "In Vivo Fast Fourier Transform Analysis of the Autofluorescence of Normal and Neoplastic Upper Aerodigestive Mucosa," *Surgical Oncology*, Vol. XLV, pp. 488-492 (1994); U.S. Pat. No. 5,042,494, inventor Alfano, which issued Aug. 27, 1991; U.S. Pat. No. 5,369,496, inventors Alfano et al., which issued November 29, 1994; U.S. Pat. No. 5,467,767, inventors Alfano et al., which issued Nov. 21, 1995, Tang et al., "Native fluorescence spectroscopic detection of the effects of chemotherapeutic retinoids on a cancer model of the aerodigestive tract," *Optics for protection of man and environment against natural and technological disasters*, G. von Bally and H. I. Bjelkhagen editors, Elsevier Science Publisher (1993); Glassman et al., "Ultraviolet Excited Fluorescence Spectra from Non-malignant and Malignant Tissues of the Gynecological Tract," *Lasers in the Life Sciences*, 5(1–2):49–58 (1992); Yang et al., "Fluorescence Spectroscopy as a Photonic Pathology Method for Detecting Colon Cancer, *Lasers in the Life Sciences*, 6(4):259–76 (1995); Schomacker et al., "Ultraviolet Laser-Induced Fluorescence of Colonic Tissue: Basic Biology and Diagnostic Potential," *Lasers in Surgery and Medicine*, 12:63–78 (1992); Richards-Kortum et al., "Spectroscopic Diagnosis of Colonic Dysplasia," *Photochemistry and Photobiology*, 53(6):777–86 (1991); Alfano et al., "Light Sheds Light on Cancer-Distinguishing Malignant Tumors from Benign Tissues and Tumors," The *Bulletin of the New York Academy of Medicine*, 67(2): 143–50 (1991); Tang et al., "Spectroscopic Differences between Human Cancer and Normal Lung and Breast Tissues," *Lasers in Surgery and Medicine*, 9:290–295 (1989); Alfano et al., "Fluorescence Spectra from Cancerous and Normal Human Breast and Lung Tissues, " *IEEE J. Quantum Electron.*, Vol. QE-23, No. 10, 1806–11 (1987); and Alfano et al., "Laser Induced Fluorescense Spectroscopy from Native Cancerous and Normal Tissue, " *IEEE J. Quantum Electron.*, Vol. QE-20, No. 12, 1507–16 (1984), all of which are incorporated herein by reference.

Although optical spectroscopy-based cancer detection techniques of the type described above possess many desirable properties as compared to other cancer detection techniques, there nevertheless remains a need for such techniques to be more sensitive and/or more specific in detecting cancer.

SUMMARY OF THE INVENTION

It is an object of the present invention to provide a novel method for detecting cancer.

It is another object of the present invention to provide a method for detecting cancer that involves the use of optical spectroscopy.

It is still another object of the present invention to provide a method for detecting cancer as described above that is more sensitive and more specific than existing cancer detection techniques.

Additional objects, as well as features, advantages and aspects of the present invention, will be set forth in part in the description which follows, and in part will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

The present invention is premised on the unexpected discovery that, using Fourier analysis, one can distinguish the native fluorescence emission spectra of cancerous tissues from those of corresponding non-cancerous tissues. This difference between cancerous and non-cancerous tissues was discovered as follows: First, cancerous, fat and normal breast tissue samples were each illuminated with light at a wavelength of approximately 300 nm. Next, the resultant fluorescence from each tissue sample was measured at 0.5 nm intervals over the spectral region from approximately 320 nm to approximately 580 nm to yield respective fluorescence emission spectra. The magnitude and phase for the first three Fourier transform harmonics were then determined for each of the fluorescence emission spectra. The present inventors noted that one could use the magnitude and phase determinations for each of the three harmonics to differentiate cancerous, fat and normal tissue samples from one another with high degrees of sensitivity and specificity. The present inventors also noted that, by using the magnitude and phase calculations obtained for two or more harmonics, the accuracy of the technique could be improved.

In view of the above, according to one aspect of the present invention, there is described a method for determining if a tissue sample is cancerous or not, said method comprising the steps of:

(a) illuminating the tissue sample with light of a wavelength suitable to cause cancer-indicative native fluorophors in the tissue sample to fluoresce;

(b) obtaining a fluorescence spectrum for the tissue sample;

(c) performing Fourier analysis on the fluorescence spectrum so as to determine respective magnitude and phase calculations for at least one Fourier harmonic; and (d) comparing the respective magnitude and phase calculations for at least one of said at least one Fourier harmonics to standards obtained from cancerous and non-cancerous tissue samples.

As can readily be appreciated, the aforementioned method is not limited to the Fourier analysis of fluorescence emission spectra and is equally applicable to the Fourier analysis of time-resolved fluorescence spectra. Moreover, it can readily be appreciated that the teachings of the present invention can analogously be applied to the Fourier analysis of fluorescence excitation spectra, as well as the Fourier analysis of other optical spectra (e.g., Raman spectra, absorption spectra, etc.). The present invention is well-suited to detecting cancer in tissue samples of various states (e.g., cancerous, pre-cancerous, benign, fat, normal, etc.) and can be used to detect cancer in various tissue types (e.g., breast, colon, GYN, gastrointestinal, aerodigestive, bladder, brain, etc.).

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

As noted above, several biological compounds which occur naturally in cells and tissues fluoresce in the ultraviolet and visible regions of the spectrum when excited with suitable wavelengths of light. Examples of these fluorescing biological compounds (also sometimes referred to herein as "fluorophors") include tryptophan, elastin, collagen, nicotinamide adenine dinucleotide (NADH), adipose, flavins and porphyrins. It has previously been found that these fluorophors fluoresce differently in cancerous tissues than in non-cancerous tissues, and many existing optical spectroscopy-based cancer detection techniques exploit this difference by comparing the fluorescence properties of cancerous and non-cancerous tissues at specific wavelengths. The large number of these fluorophors, however, makes difficult the comparison of fluorescence spectra (as opposed to fluorescence at specific wavelengths) from cancerous and non-cancerous tissues. The present invention provides a framework for comparing the fluorescence spectra from cancerous and non-cancerous tissues and for providing a diagnostic tool for determining whether a tissue sample is cancerous or not based on its fluorescence spectra. This is accomplished, as will hereinafter be described in greater detail, by using Fourier analysis to compare the fluorescence spectra derived from cancerous and non-cancerous tissues.

A total of 224 breast tissue samples - 97 malignant, 61 normal and 66 fat—were obtained from dissected specimens obtained from St. Vincent Medical Center of Staten Island. The samples were not chemically treated prior to the spectroscopic measurements discussed below. The samples, which were of random shape, were each mounted in a quartz cuvette. Fluorescence emission spectra measurements were taken for each sample using a CD-Scan™ automated lamp-based spectrophotometer (Mediscience Technology Corp., Cherry Hill, N.J.). The scan parameters were identical for all samples. Each sample was excited at 300 nm. The excitation band width was set to 4 nm. The emission intensity was measured from 320 nm to 580 nm. The emission monochrometer resolution was also set to 4 nm. The spacing of the data points was every 0.5 nm, therefore resulting in a total of 521 data points in each spectrum. The spectrophotometer employed a 16 bit analogue-to-digital converter. A digital 19 point binomial smoothing function was performed by the spectrophotometer prior to data transfer to a personal computer as a long (32 bit) integer with a scaling factor. The spectrophotometer corrected the emission intensity for fluctuations in excitation power and spectral sensitivity of the instrument. (As can readily be appreciated, excitation wavelengths other than 300 nm, such as 320 nm, 340 nm, 350 nm, etc., and corresponding spectral emission bands could be used to measure native fluorescence.) For example, one could illuminate the tissue sample at a wavelength of approximately 340 nm and measure the fluorescence emitted therefrom over the spectral band from about 350 nm to about 600 nm or could illuminate at approximately 325 nm and measure over the spectral band from about 340 nm to about 600 nm or could illuminate at approximately 310 nm and measure over the spectral band from about 340 nm to about 600 nm or could illuminate at approximately 350 nm and measure over the spectral band from about 360 nm to about 600 nm. One could also illuminate a tissue sample at an appropriate wavelength and measure fluorescence emitted therefrom over a spectral band from about 300 nm to about 488 nm. Alternatively, one could obtain an excitation spectrum of a tissue sample, for example, by exciting the tissue sample with light over the spectral region from about 250 nm to about 330 nm and measuring the resultant fluorescence therefrom at about 340 nm or by exciting with light over the spectral region from about 250 nm to about 330 nm and measuring the resultant fluorescence therefrom at about 380 n=or by exciting with light over the spectral region from about 250 rim to about 330 nm and measuring the resultant fluorescence therefrom at about 440 nm.

Figure 1:
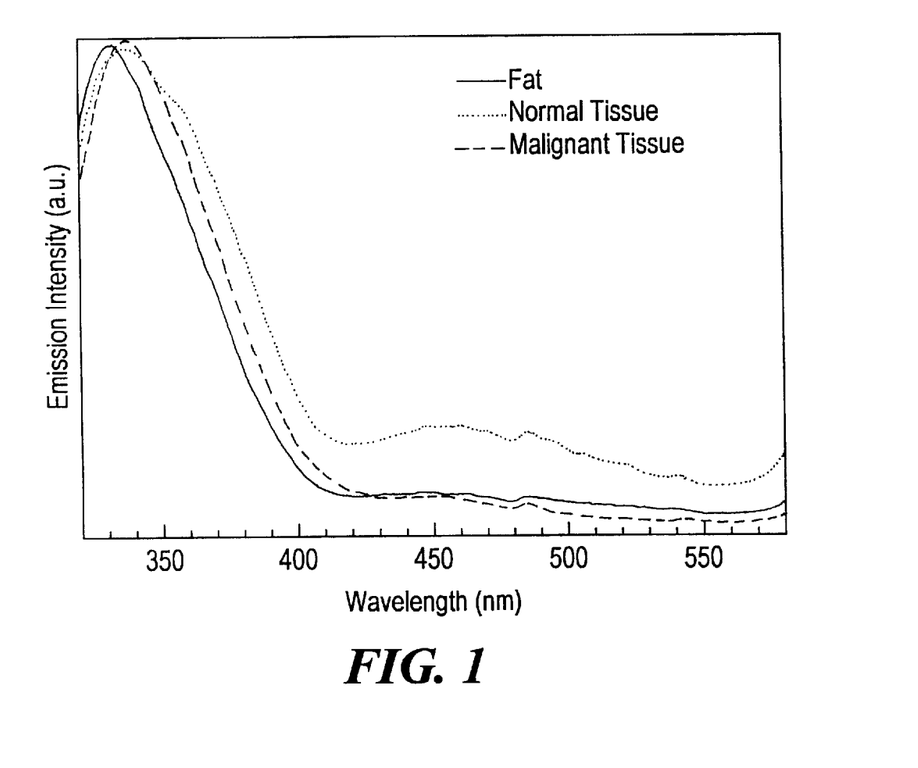
FIG. 1 is a graphic representation of average fluorescence emission spectra for 97 malignant, 61 normal and 66 fat human breast tissue samples obtained in the manner set forth in the present specification.

The average emission spectra for the three tissue types (malignant, fat and normal) are shown as three curves in FIG. 1. The curve from each sample was normalized to unit area prior to computing the respective averages. Some significant features that can be drawn from a comparison of the three curves shown in FIG. 1 are as follows: (1) The peak emission from the fat curve is shifted to shorter wavelengths than the respective peak emissions for the normal and malignant curves; (2) The 340 nm emission band of the normal curve is broader than the corresponding 340 nm emission bands for the fat and malignant curves; and (3) The relative emission intensity of the normal curve at 440 nm is greater than the relative emission intensity of the fat or malignant curves at 440 nm. This last feature is evocative of the $I_{340nm}/I_{440nm}$ ratio test disclosed in U.S. Pat. No. 5,131,398. Said ratio test successfully distinguished normal tissue from malignant tissue in 60 of 61 normal samples and 92 of 97 malignant samples (for a sensitivity of 0.95); however, said test also sometimes misidentified fat tissue as malignant tissue. Accordingly, as described below, Fourier analysis was applied to the fluorescence spectra of the 224 samples as a means of distinguishing cancerous, fat and normal tissue samples.

Before describing the results of Fourier analysis to the 224 spectral curves obtained in the manner described above, it may be helpful to provide some discussion of Fourier analysis. The Fourier transform is well known for a piece-wise continuous function, f(t). and is defined by:

$$F(\omega) = \int_{-\infty}^{\infty} f(t) e^{-i\omega t} d\omega \qquad (1)$$

Although t and $\omega$ usually refer to the time and frequency domain, they can be any Fourier transform pair, such as position and momentum. For the spectra under consideration, t is wavelength and will be replaced by the symbol $\lambda$, while $\omega$ represents the spatial frequency components of the spectra, not the optical frequency.

From Equation (1), it is observed that a translation in t-space gives a phase shift in $\omega$ space. This property of Fourier transforms can be used to distinguish spectra that have somewhat similar shapes but are shifted in wavelength.

In making real measurements, one does not have a continuous function.$f(\lambda)$; instead, one usually samples the data at fixed intervals. If the sampling interval is $\Lambda_0$, the maximum frequency component of the sampled signal is $f_m = 1/(2\Lambda_0)$. One then defines a discrete Fourier transform as:

$$F_k(\omega) = \frac{1}{n} \sum_{j=0}^{j=n-1} f_j e^{\frac{-i2\pi jk}{n}} = \qquad (2)$$

$$\frac{1}{n} \sum_{j=0}^{j=n-1} f_j \left( \cos\left[\frac{2\pi jk}{n}\right] + i\sin\left[\frac{2\pi jk}{n}\right] \right)$$

where n is the number of data points, j is the index of the intensity data, $i = \sqrt{-1}$, and $k = 0, 1, 2, \ldots n-1$ are the equally spaced harmonics and include both positive and negative frequencies with the highest harmonic being $n/2$. The negative frequency components are given by $k = n/2 \ldots n-1$. For $f(\lambda)$ real, $F(\omega)$ is hermetian; therefore, only the positive frequency components need be computed. In this case, the Fourier coefficients (except for the D.C.) are multiplied by 2 to include both the positive and negative frequencies. It is noted that one can compute any desired harmonic without calculating the entire Fourier spectrum.

The emission spectra that were analyzed each consisted of 521 data points. The function $f_j(\lambda)$ represents the signal (fluorescence intensity) at each wavelength, i.e., $f_0$ is the intensity of the first data point (320 nm), $f_1$ is the intensity at second data point (320.5 nm), $f_{520}$ is the intensity at the last data point (580 nm), etc. Therefore, each discrete Fourier transform consists of the D.C. component and 260 positive frequency harmonics. However, the monochrometer resolution and the data smoothing function both performed a low pass filtering operation, so only the lower order harmonics were investigated. In this analysis, the magnitude and phase of the DC and first three harmonics were calculated on a personal computer using an algorithm based on Equation (2). In this calculation, first the real and imaginary parts of the Fourier coefficients were calculated from Equation (2). The real and imaginary parts of the D.C. and first three harmonics are shown explicitly as:

$$F_0 = \frac{1}{n} \sum_{j=0}^{j=n-1} f_j \qquad (3)$$

$$F_1 = F_{1R} + iF_{1I} = \frac{2}{n} \sum_{j=0}^{j=n-i} f_j \left( \cos\left[\frac{2\pi j}{n}\right] + i\sin\left[\frac{2\pi j}{n}\right] \right)$$

$$F_2 = F_{2R} + iF_{2I} = \frac{2}{n} \sum_{j=0}^{j=n-1} f_j \left( \cos\left[\frac{4\pi j}{n}\right] + i\sin\left[\frac{4\pi j}{n}\right] \right)$$

$$F_3 = F_{3R} + iF_{3I} = \frac{2}{n} \sum_{j=0}^{j=n-1} f_j \left( \cos\left[\frac{6\pi j}{n}\right] + i\sin\left[\frac{6\pi j}{n}\right] \right)$$

where $F_{kR}$ is the real part, and $F_{kI}$ is the imaginary part of the Fourier- coefficient. It is observed that the zero order harmonic (D.C. component) is real and equal to the average value of $f(\lambda)$. The magnitude and phase of the $k^{th}$ is then computed by $$M_k = [F_{kR}^2 + F_{kI}^2]^{\frac{1}{2}} \qquad (4)$$

$$\Phi_k = \tan^{-1}\left[\frac{F_{kI}}{F_{kR}}\right]$$

All calculations were performed using double precision floating point variables (8 bytes per intensity value). To correct for any variation in collection efficiency due to geometric, or other factors, all magnitudes were normalized by dividing by the D.C. component. This is equivalent to normalizing all spectral curves to unit area.

As can be seen from the results set forth in TABLE I below, there were significant differences in the magnitude and phase of the Fourier transform data for the 224 tissue samples described above. In particular, the phase (given in degrees) of the first three harmonics for the fat tissue samples was significantly smaller than that for the malignant and normal tissue samples. In addition, the magnitude (normalized by dividing by the D.C. component) of the first three harmonics for the normal samples was smaller than that for the malignant and fat samples.

TABLE I

|  | Normal | Fat | Malignant |
| --- | --- | --- | --- |
| Relative magnitude of $1^{st}$ harmonic | 0.94 ± 0.17 | 1.267 ± 0.10 | 1.37 ± 0.10 |
| Relative magnitude of $2^{nd}$ harmonic | 0.72 ± 0.11 | 0.94 ± 0.057 | 0.95 ± 0.07 |
| Relative magnitude of $3^{rd}$ harmonic | 0.33 ± 0.08 | 0.55 ± 0.058 | 0.52 ± 0.06 |
| Phase of $1^{st}$ harmonic | 50.41 ± 6.32 | 41.34 ± 2.63 | 47.34 ± 2.15 |
| Phase of $2^{nd}$ harmonic | 82.77 ± 5.72 | 72.28 ± 4.02 | 80.07 ± 3.08 |
| Phase of $3^{rd}$ harmonic | 108.93 ± 3.20 | 92.95 ± 6.24 | 103.74 ± 3.20 |

Using the data presented above, one can determine if a tissue sample is cancerous, as opposed to fat or normal, by employing the following method: First, the magnitude and phase of the Fourier coefficients of the tissue sample are determined. Next, the magnitude of the tissue sample is compared to standards to determine if the tissue sample is normal, as opposed to fat or malignant. Finally, the phase of the tissue sample is compared to standards to determine if the tissue sample is fat or malignant. This comparison process can be accomplished either by determining the distribution of data points based on data from large numbers of known samples and calculating probabilities or by setting threshold values for the magnitude and phase. Making a comparison by setting threshold values does not require a mathematical model of the distribution. Thresholding can be understood with the help of FIG. 2—a Cartesian plot of magnitude versus phase defining four zones or quadrants. If the magnitude is above a determined threshold (i.e., Zones 1 and 4), the sample is either malignant or fat. If the magnitude is below a determined threshold (i.e., Zones 2 and 3), the sample is either normal or fat. If the phase is above a determined threshold (i.e., Zones 1 and 2), the sample is either malignant or normal. If the phase is below a determined threshold (i.e., Zones 3 and 4), the sample is either fat or normal. Combining the magnitude and phase thresholds, all samples above the threshold in both magnitude and phase are malignant and lie in Zone 1. All normal samples lie in Zones 2 or 3, and all fat samples lie in Zones 3 or 4.

Application of the foregoing principles to the first three harmonics of the 224 samples discussed above are summarized below.

First Harmonic

Figure 3:
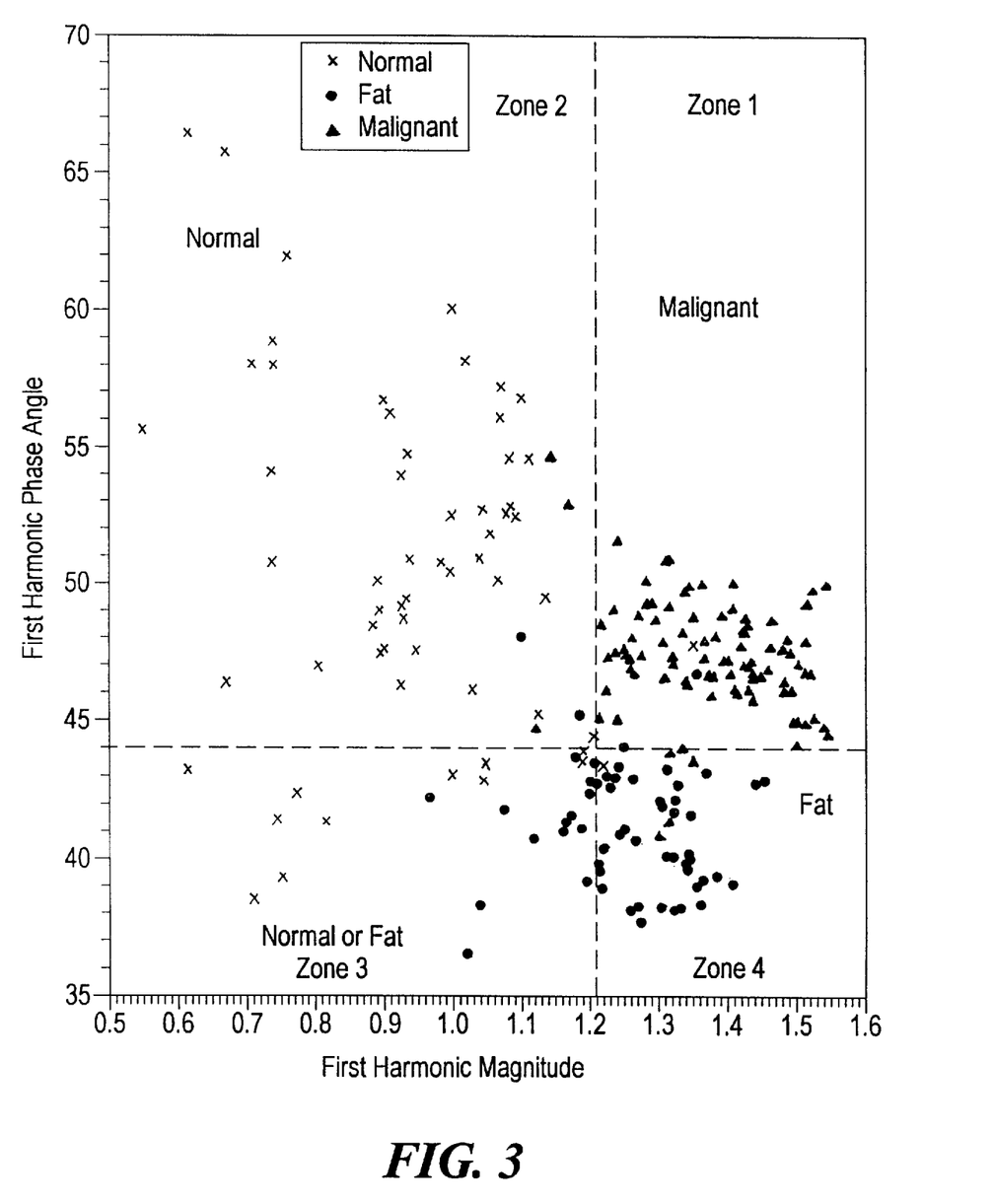
FIG. 3 is a graphic representation of the thresholding technique of FIG. 2 applied to the first harmonic for a collection of normal, fat and malignant human breast tissue samples.
Figure 4A:
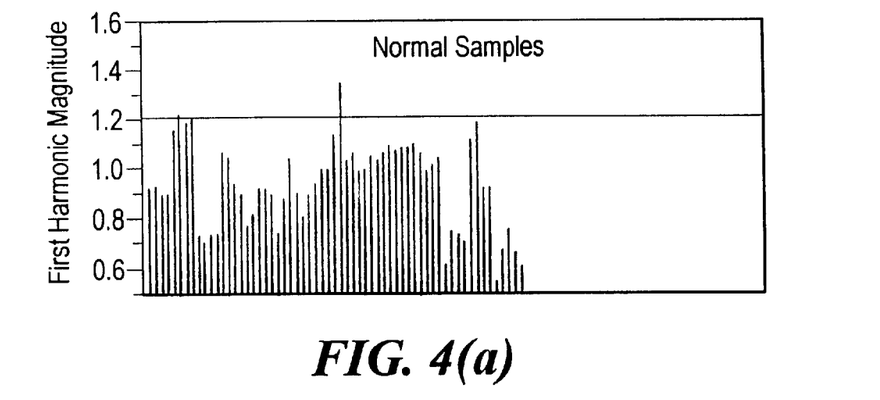
FIGS. 4(a) through 4(c) are histograms of the first harmonic magnitude for the normal, fat and malignant human breast tissue samples, respectively, of FIG. 3.
Figure 4B:
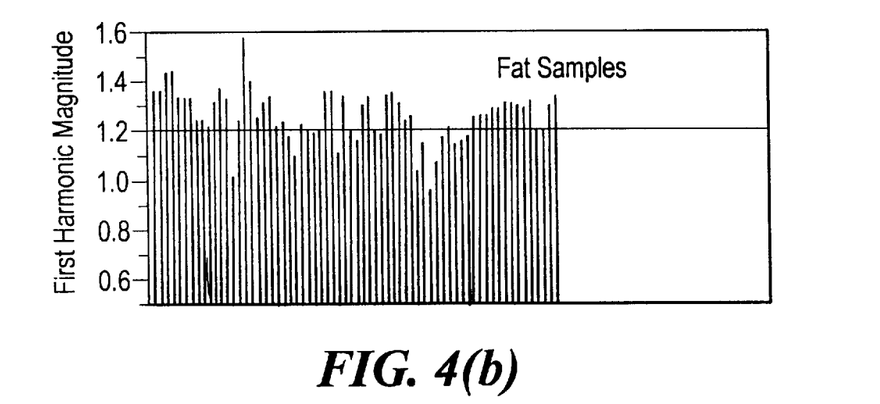
Figure 4C:
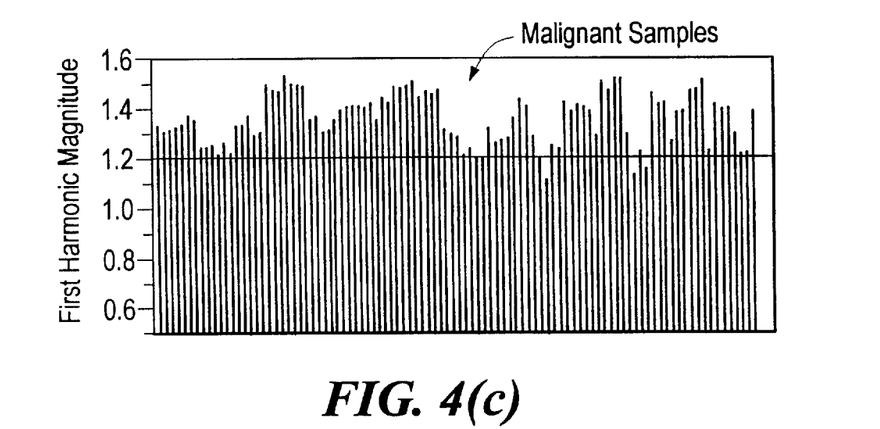
Figure 5A:
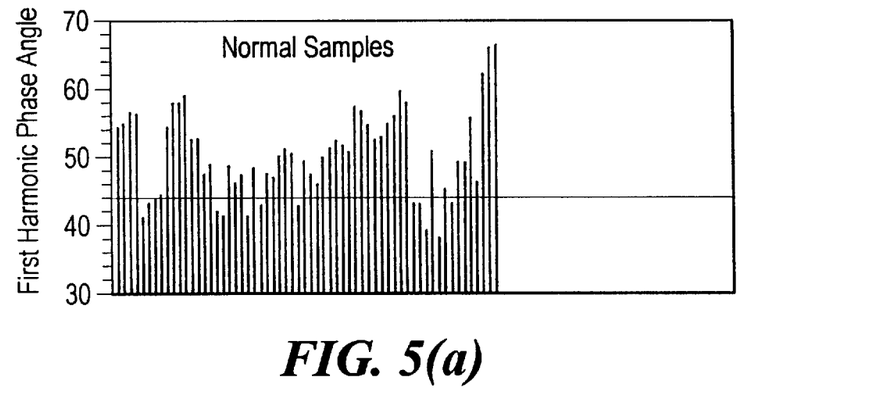
FIGS. 5(a) through 5(c) are histograms of the first harmonic phase for the normal, fat and malignant human breast tissue samples, respectively, of FIG. 3.
Figure 5B:
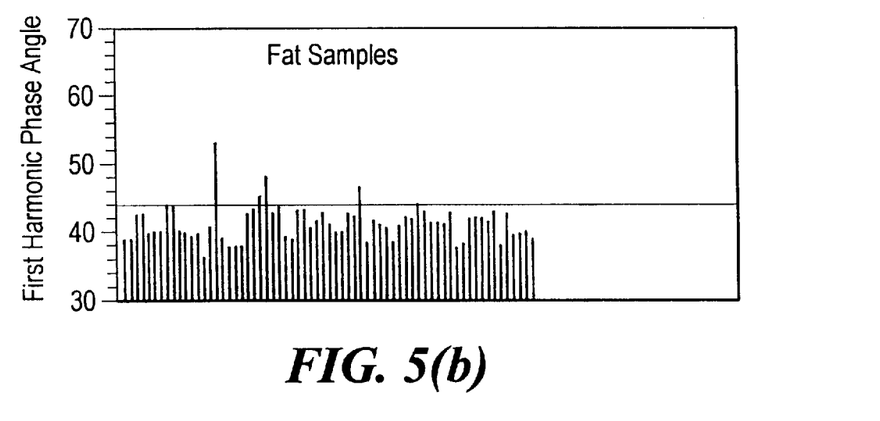
Figure 5C:
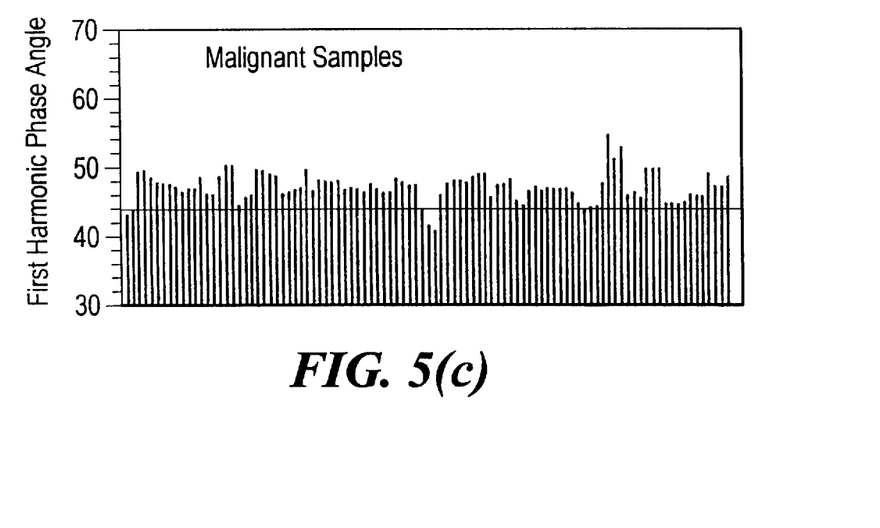

The magnitude and phase results for the first harmonic are graphically represented in FIG. 3. By setting threshold values of 1.21 for the magnitude and 44° for the phase, 89 of 97 malignant samples (located in Zone 1) were correctly identified for a sensitivity of 0.92. Three of the malignant samples were misdiagnosed as normal (Zone 2) and five as fat (Zone 4). No malignant samples were located in Zone 3, which would indicate that they did not meet both the magnitude and phase thresholds. These threshold limits also gave a total of 5 false positives for a specificity of 0.96. (In calculating specificity, statistics for normal and fat tissue samples were combined.) One normal sample was misidentified as fat (Zone 4) and two fat samples were misidentified as normal tissue (Zone 2). Histograms of the first harmonic magnitude for the normal, fat and malignant tissue samples are shown in FIGS. 4(a) through 4(c), respectively, and histograms of the first harmonic phase for the normal, fat and malignant tissue samples are shown in FIGS. 5(a) through 5(c), respectively.

Figure 2:
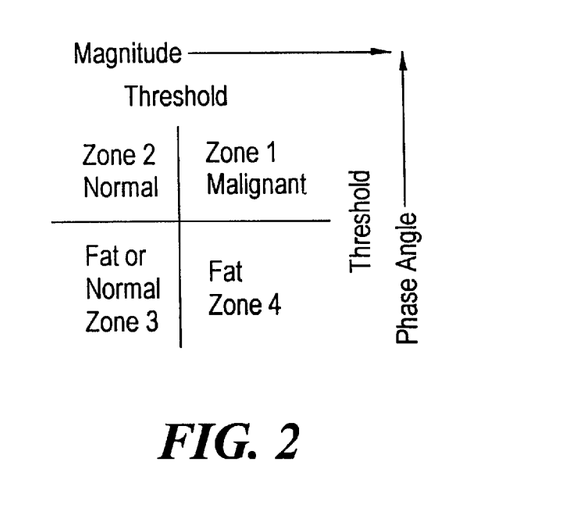
FIG. 2 is a graphic zone representation of the thresholding technique described in the present specification.

If, instead of using the thresholding technique of FIG. 2 to differentiate the various samples, one considers the magnitude and phase for the samples to be variables with Gaussian distributions, with the mean and standard deviation as given in Table 1, then 88 of 97 malignant samples were correctly identified for a sensitivity of 0.91. Two fat samples were misclassified as malignant and three fat samples were misclassified as normal. One normal sample was misclassified as malignant and six normal samples were misclassified as fat, for a specificity of 0.98.

Second Harmonic

Figure 6:
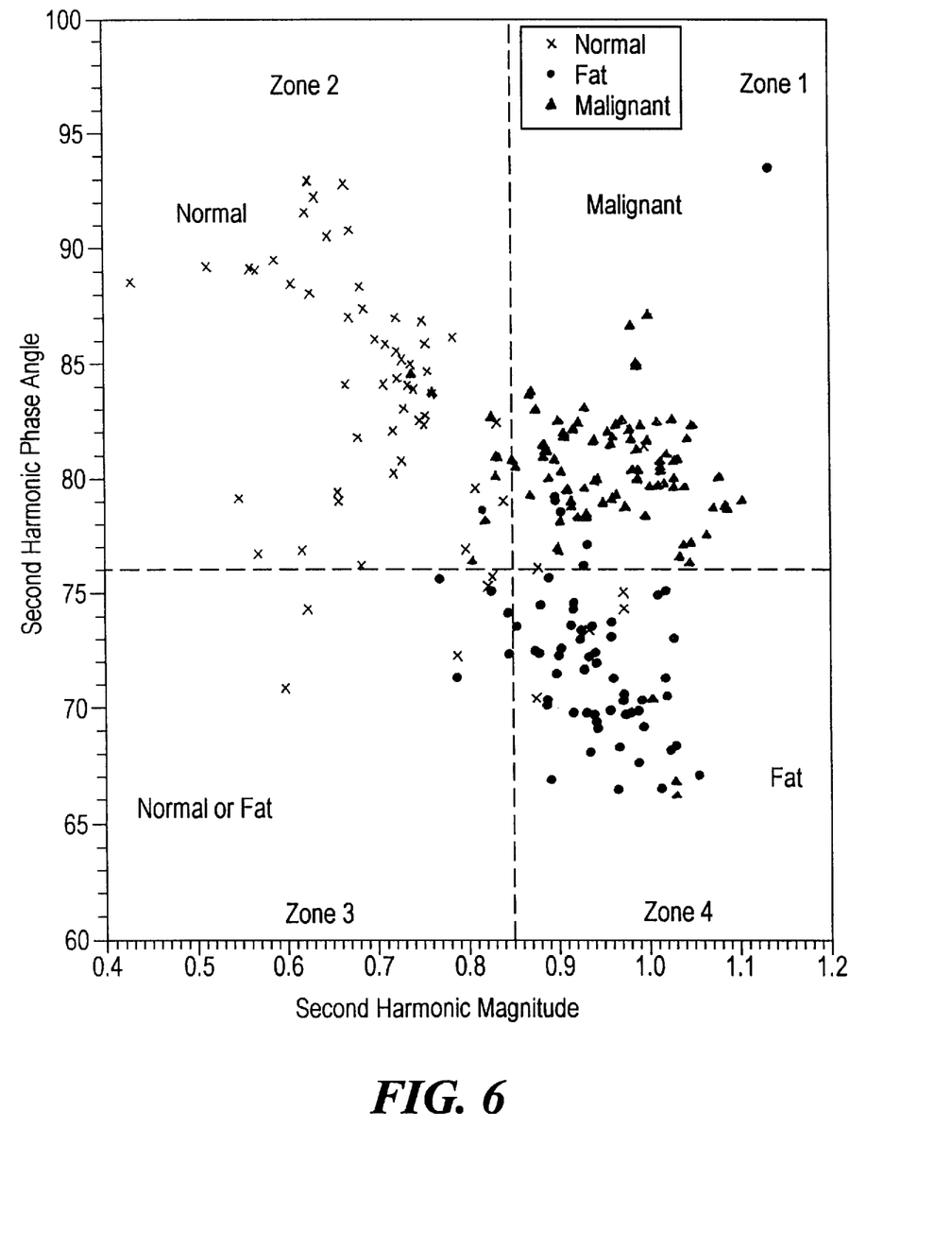
FIG. 6 is a graphic representation of the thresholding technique of FIG. 2 applied to the second harmonic of the same collection of normal, fat and malignant human breast tissue samples used in FIG. 3.
Figure 7A:
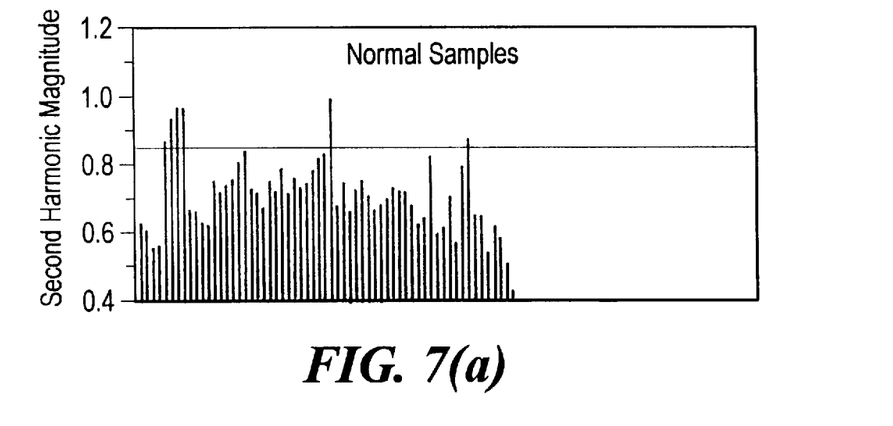
FIGS. 7(a) through 7(c) are histograms of the second harmonic magnitude for the normal, fat and malignant human breast tissue samples, respectively, of FIG. 6.
Figure 7B:
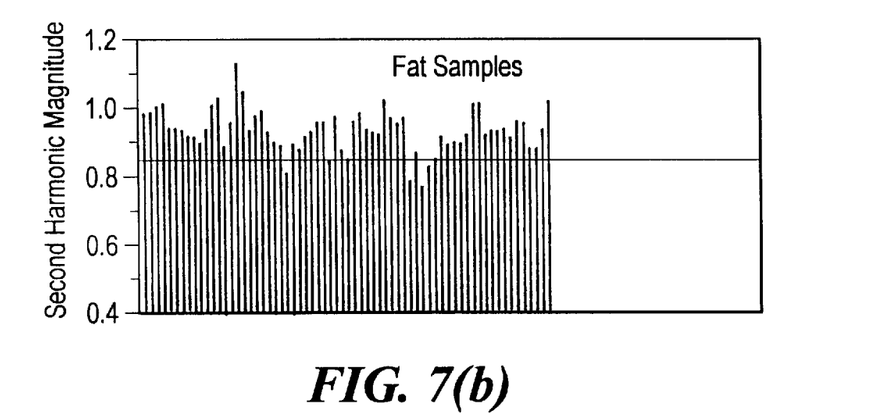
Figure 7C:
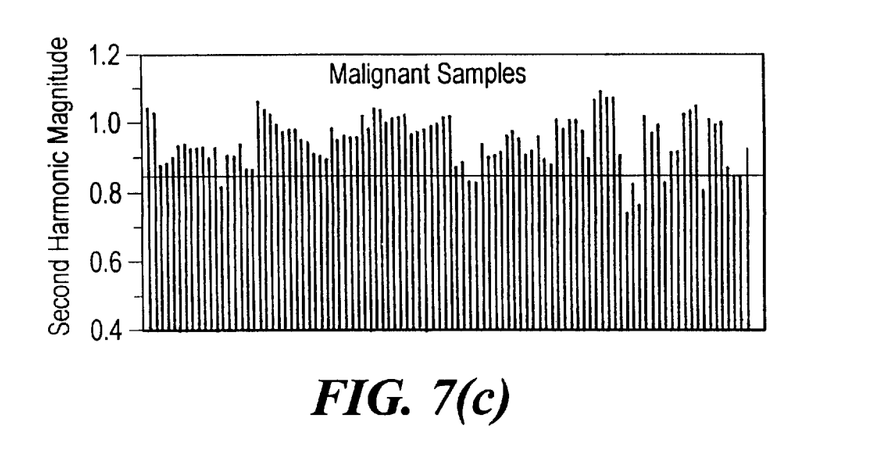
Figure 8A:
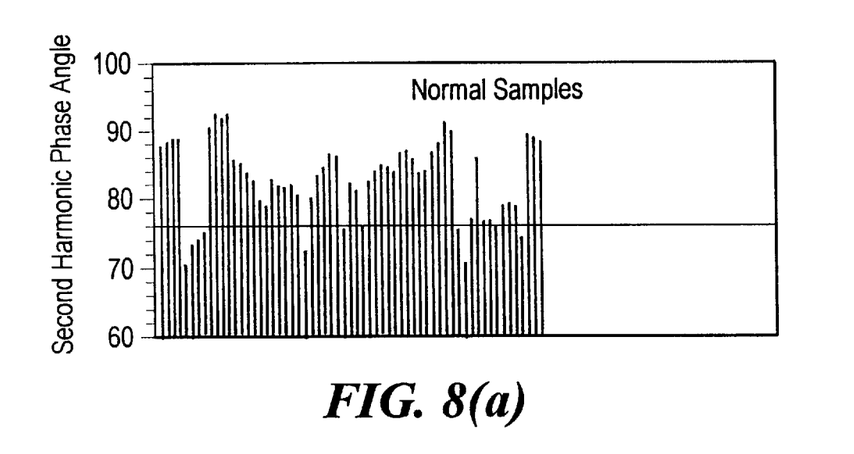
FIGS. 8(a) through 8(c) are histograms of the second harmonic phase for the normal, fat and malignant human breast tissue samples, respectively, of FIG. 6.
Figure 8B:
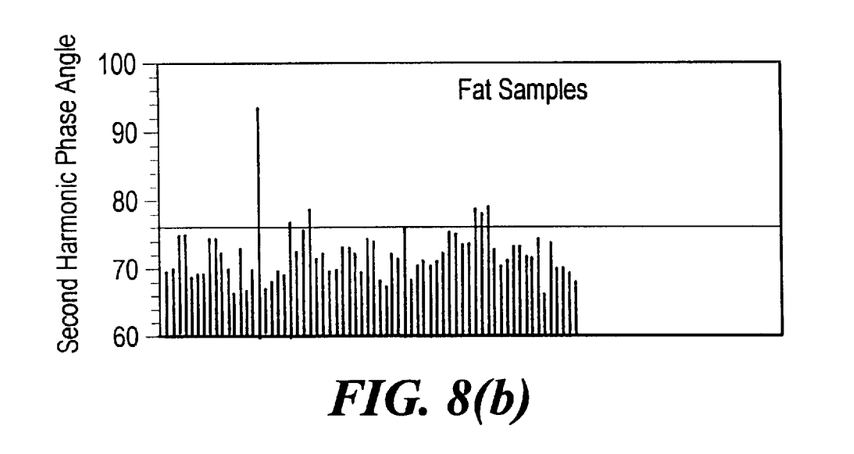
Figure 8C:
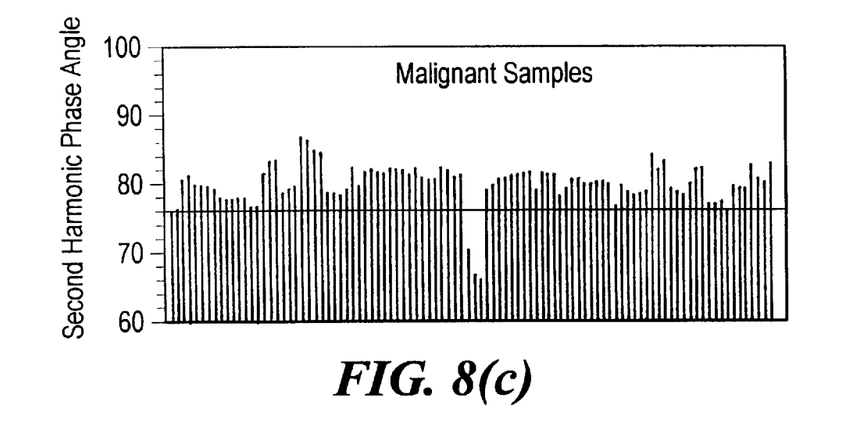

Referring now to FIG. 6, there is shown a graphic representation of the data for the second Fourier coefficient in accordance with the thresholding technique described above. Applying a magnitude threshold value of 0.85, and a phase threshold of 76°, 87 of 97 malignant samples were correctly identified (Zone 1) for a sensitivity of 0.90. Seven malignant samples were located in Zone 2 (and misdiagnosed as normal) and three malignant samples were located in Zone 4 (and misdiagnosed as fat). None were in Zone 3. Two normal samples were misidentified as malignant (Zone 1) and four normal samples were misidentified as fat (Zone 4). Six fat samples were misidentified as malignant (Zone 1), and one fat sample was misidentified as normal (Zone 2), for a specificity of 0.94. Histograms of the second harmonic magnitude for the normal, fat and malignant tissue samples are shown in FIGS. 7(a) through 7(c), respectively, and histograms of the second harmonic phase for the normal, fat and malignant tissue samples are shown in FIGS. 8(a) through 8(c), respectively.

Again, if a Gaussian distribution is used instead of thresholding, 89 of 97 malignant samples were correctly identified, for a sensitivity of 0.92. Four fat samples were misclassified as malignant and three as normal. Two normal samples were misclassified as malignant and seven as fat. The total of six false positives out of 127 normal and fat samples yields a specificity of 0.95

Third Harmonic

Figure 9:
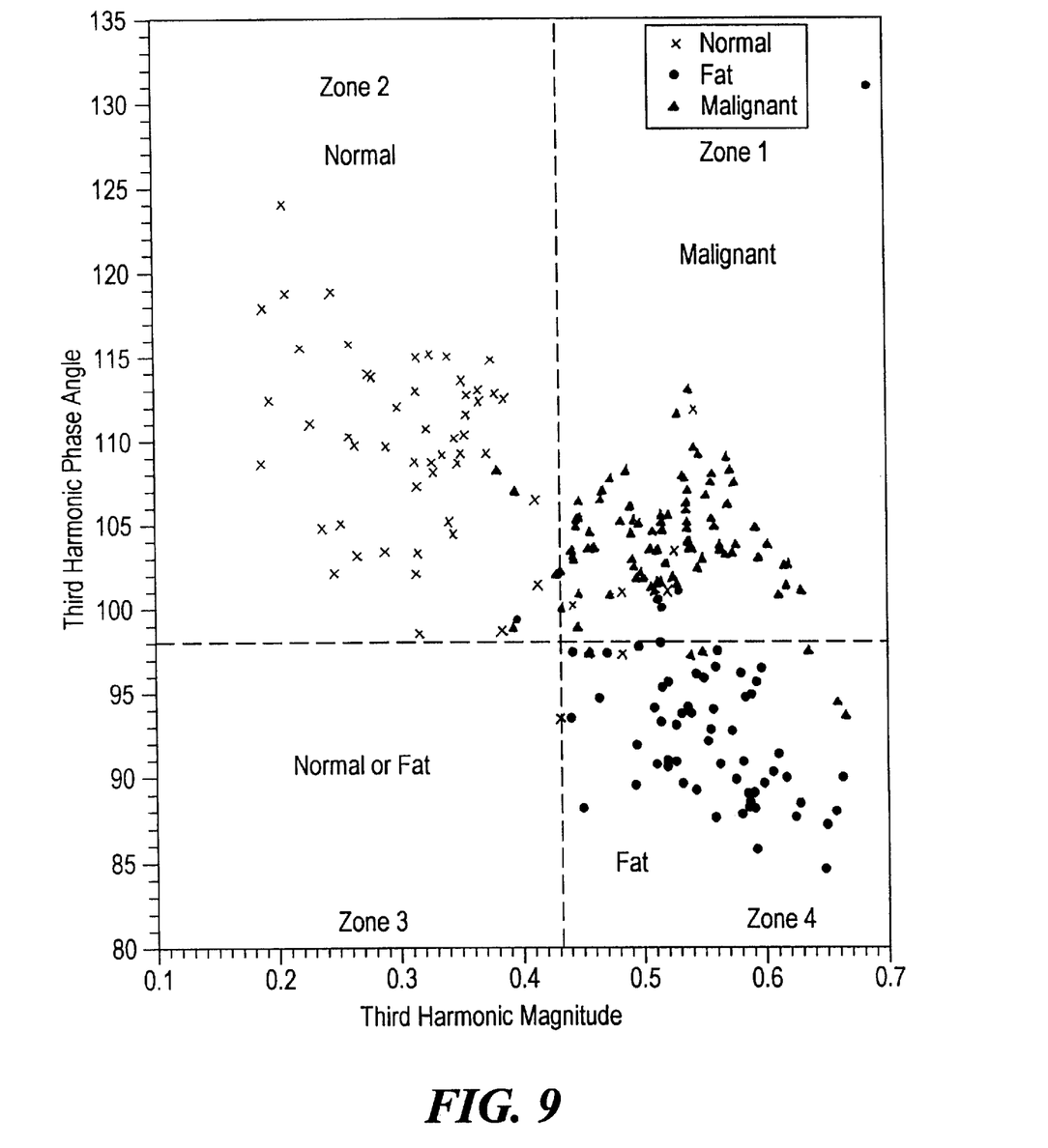
FIG. 9 is a graphic representation of the thresholding technique of FIG. 2 applied to the third harmonic of the same collection of normal, fat and malignant human breast tissue samples used in FIG. 3.
Figure 10A:
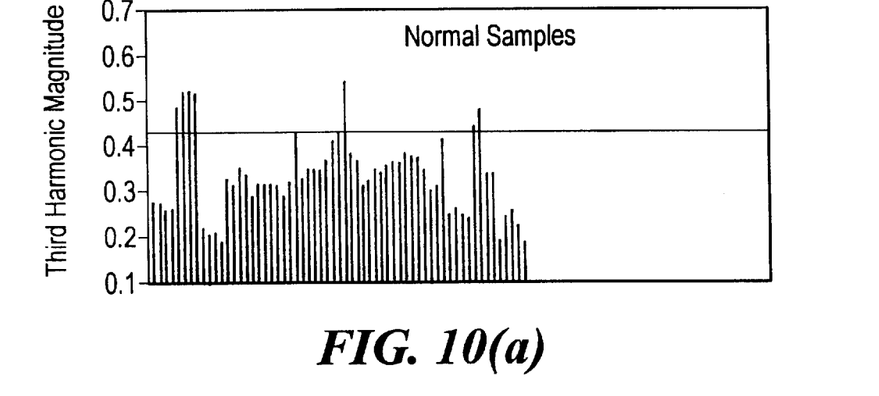
FIGS. 10(a) through 10(c) are histograms of the third harmonic magnitude for the normal, fat and malignant human breast tissue samples, respectively, of FIG. 9.
Figure 10B:
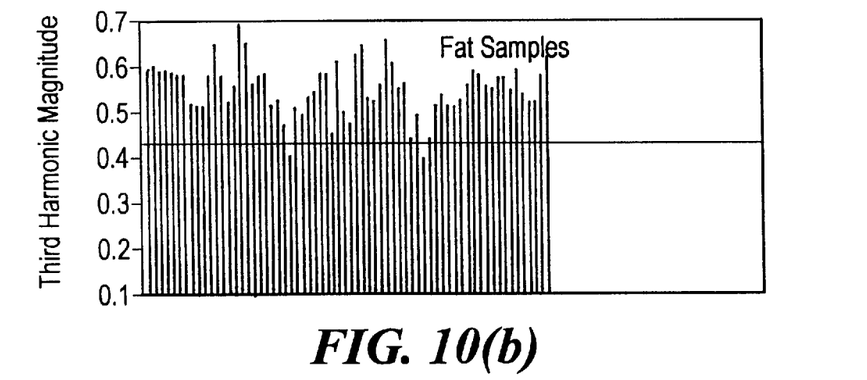
Figure 10C:
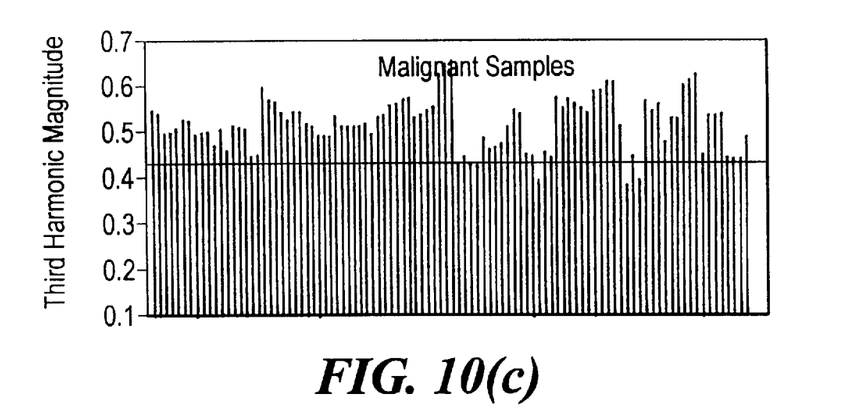
Figure 11A:
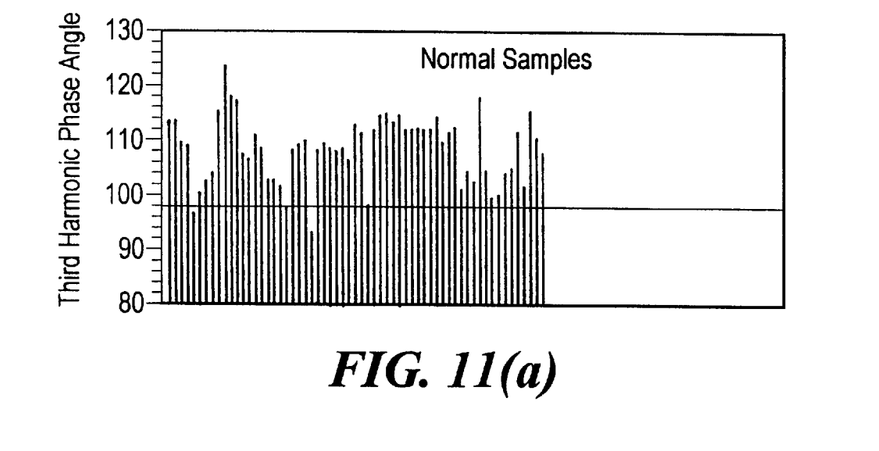
FIGS. 11(a) through 11(c) are histograms of the third harmonic phase for the normal, fat and malignant human breast tissue samples, respectively, of FIG. 9.
Figure 11B:
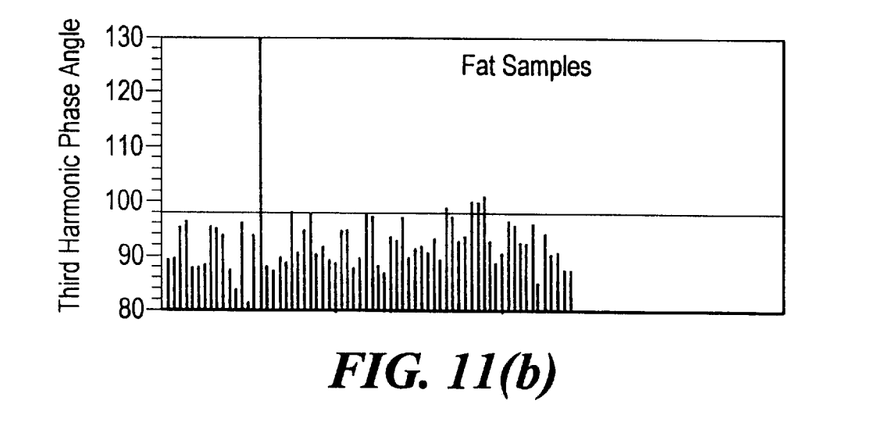
Figure 11C:
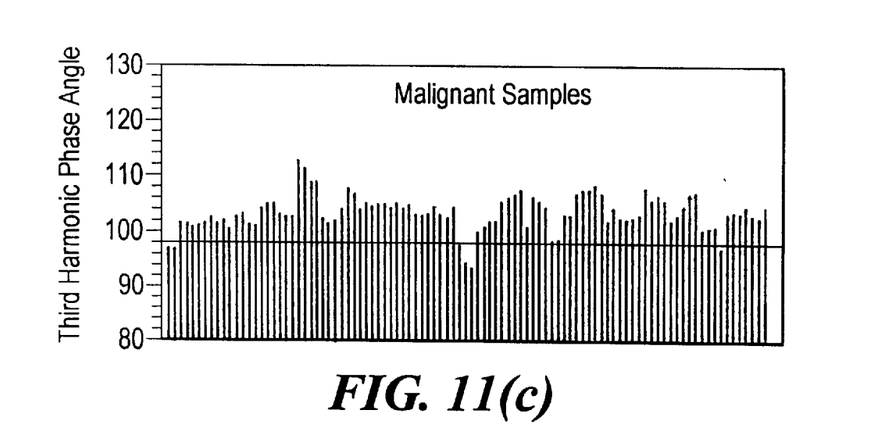

Referring now to FIG. 9, there is shown a graphic representation of the data for the third Fourier coefficient in accordance with the thresholding technique described above. Applying a magnitude threshold value of 0.43, and a phase threshold of 98°, 87 of 97 malignant samples were correctly identified (Zone 1) for a sensitivity of 0.90. Six of the malignant samples were misdiagnosed as fat (Zone 4) and four as normal (Zone 2). Nine normal samples were misidentified, seven as malignant (Zone 1) and two as fat (Zone 4). Six fat samples were misidentified, five as malignant (Zone 1) and one as normal (Zone 2). The total of 12 false positives resulted in a specificity of 0.90. Histograms of the third harmonic magnitude for the normal, fat and malignant tissue samples are shown in FIGS. 10(a) through 10(c), respectively, and histograms of the second harmonic phase for the normal, fat and malignant tissue samples are shown in FIGS. 11(a) through 11(c), respectively.

Again, if a Gaussian distribution is used instead of thresholding, 87 of 97 malignant samples were correctly identified, for a sensitivity of 0.92. There were also ten false positives—seven normal samples and three fat samples—for a specificity of 0.92. In addition, two normal samples were mistakenly identified as fat samples and three fat samples were mistakenly identified as normal samples.

In reviewing the above results, the present inventors have noted that those samples which gave false results on one of the harmonic tests were more likely to give false results on another harmonic test. One solution devised by the present invention to improve the accuracy of the present technique (by reducing the frequency of false positive results) is to combine the results of the three harmonic tests. One way of combining the results of the three harmonic tests is to assign each sample a score of +1 if diagnosed as malignant or 0 if diagnosed as normal or fat, for each harmonic test. The scores for the three harmonic tests can then be added to give each sample a total score of 0, 1, 2 or 3. Applying this approach to the misdiagnosed samples, it is noted that three of the malignant samples failed only 1 of the 3 tests, five failed 2 of the 3 tests and five failed all 3 tests. Therefore, of the 97 malignant samples, five samples each received a total score of 0, another five samples each received a total score of 1, another three samples each received a total score of 2, and the remaining 84 samples each received a total score of 3. For the normal tissue samples, only one gave a false positive on all three tests (total score=3), one sample gave a false positive on 2 of the 3 tests (total score=2), five samples reported false positives on only 1 of the 3 tests (total score=1), and the remaining 54 normal samples received a total score of 0. For the fat samples, one sample failed all three tests (total score=3), five samples failed 2 of the 3 tests (total score=2), two samples failed only 1 of the 3 tests (total score=1), and the remaining 58 samples received a total score of 0.

Accordingly, if the decision to classify a sample as malignant is to decided by a positive result on only one of the three harmonic tests (i.e., requiring a score of 1), there would be five false negatives (out of 97 samples) and 15 false positives (out of 127 samples), for a sensitivity of 0.95 and a specificity of 0.88. If a diagnosis of malignancy is to be decided by a total score of 2 (i.e., testing positive on 2 out of the 3 harmonic tests), then the above results would give 10 false negatives and 8 false positives, for a sensitivity of 0.90 and a specificity of 0.94. If, however, a diagnosis of malignancy requires a positive result on all three tests (total score=3), there would be 13 false negatives but only two false positives, for a sensitivity of 0.86 and a specificity of 0.98. As can readily be seen, requiring a higher score on the three tests for a diagnosis of malignancy reduces test sensitivity while increasing test specificity.

Test accuracy can also be improved by combining the three harmonic classification results from assumed Gaussian distributions. According to this approach, 89 of 97 malignant samples were correctly classified, for a sensitivity of 0.92. Five normal samples were incorrectly classified as fat and two normal samples were incorrectly classified as malignant. Three fat samples were incorrectly identified as normal and one normal sample was incorrectly identified as malignant, giving a total of three false positives for a specificity of 0.98. The statistical results for the $1^{st}$, $2^{nd}$ and $3^{rd}$, as well as the combined tests are summarized below in Table II. (Specificity statistics combine normal and fat tissue results.)

TABLE II

|  | Threshold | | Gaussian Distribution | |
| --- | --- | --- | --- | --- |
|  | Sensitivity | Specificity | Sensitivity | Specificity |
| $1^{st}$ harmonic | 0.92 | 0.96 | 0.91 | 0.98 |
| $2^{nd}$ harmonic | 0.90 | 0.94 | 0.92 | 0.95 |
| $3^{rd}$ harmonic | 0.90 | 0.90 | 0.92 | 0.92 |
| Combined results (Score = 1) | 0.95 | 0.88 | | |
| Combined results (Score = 2) | 0.90 | 0.94 | | |
| Combined results (Score = 3) | 0.86 | 0.98 | 0.92 | 0.98 |

Table III summarizes the zone locations for the 3 harmonic scatter plots. (Malignant tissues should lie in the first zone, normal tissue in the second or third zones and fat tissue in the third or fourth zones.)

TABLE III

| | | Zone | | | |
| --- | --- | --- | --- | --- | --- |
| Harmonic | Tissue Type | First | Second | Third | Fourth |
| $1^{st}$ Harmonic | Normal | 1 | 47 | 12 | 1 |
| | Fat | 4 | 2 | 14 | 46 |
| | Malignant | 89 | 3 | 0 | 5 |
| $2^{nd}$ Harmonic | Normal | 2 | 50 | 5 | 4 |
| | Fat | 6 | 1 | 3 | 56 |

TABLE III-continued

| | | Zone | | | |
| --- | --- | --- | --- | --- | --- |
| Harmonic | Tissue Type | First | Second | Third | Fourth |
| | Malignant | 87 | 7 | 0 | 3 |
| $3^{rd}$ Harmonic | Normal | 7 | 52 | 0 | 2 |
| | Fat | 5 | 1 | 1 | 59 |
| | Malignant | 87 | 4 | 0 | 6 |

As can be seen, combining the results of multiple harmonics can be used to increase accuracy. If a threshold approach is used to make a diagnosis, the use of multiple harmonics can either increase sensitivity by requiring a lower score (i.e., a positive result for fewer harmonics) or increase specificity (i.e., a positive result on more harmonics). The trade-off is that increasing sensitivity can decrease specificity and vice versa. This is an unavoidable result of the binary nature of thresholding the outcome. Combining multiple tests using Gaussian distributions to make a diagnosis based on the most likely outcome for each test, however, does not suffer from this same disadvantage. The combined results of the three harmonics, using Gaussian distributions, gave a sensitivity and specificity higher than any one harmonic. Increased diagnostic accuracy may also be achieved by using a different distribution function for the magnitude or phase values.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method for determining if a tissue sample is cancerous or not, said method comprising the steps of:
   (a) illuminating the tissue sample with light of a wavelength suitable to cause cancer-indicative native fluorophors in the tissue sample to fluoresce;
   (b) obtaining a fluorescence spectrum for the tissue sample;
   (c) performing Fourier analysis on the fluorescence spectrum so as to determine respective magnitude and phase calculations for at least one non-zero order Fourier harmonic; and
   (d) comparing the respective magnitude and phase calculations for at least one of said at least one non-zero order Fourier harmonics to both a magnitude threshold and a phase threshold, both of which have been determined from known cancerous and non-cancerous tissue samples, said magnitude threshold separating cancerous magnitude values on one side thereof from non-cancerous magnitude values on an opposite side thereof, said phase threshold distinguishing cancerous phase values on one side thereof from non-cancerous phase values on an opposite side thereof whereby cancer is indicated only by the occurrence of a magnitude calculation for the tissue sample consistent with a cancerous magnitude, together with a phase calculation for the tissue sample consistent with a cancerous phase.

2. A method of determining if a tissue sample is a cancerous tissue sample as opposed to a fat tissue sample or a normal tissue sample, said method comprising the steps of:
   (a) illuminating the tissue sample with light of a wavelength suitable to cause cancer-indicative native fluorophors in the tissue sample to fluoresce;

(b) obtaining a fluorescence spectrum for the tissue sample;

(c) performing Fourier analysis on the fluorescence spectrum so as to determine respective magnitude and phase calculations for a non-zero order Fourier harmonic; and (d) comparing the respective magnitude and phase calculations for said non-zero order Fourier harmonic to standards obtained from known cancerous, fat and normal tissue samples of the same tissue type, said comparing step comprises the steps of:

(i) representing, by the respective magnitude and phase calculations for said non-zero order Fourier harmonic, each of said known cancerous, fat and normal tissue samples on a Cartesian plot having a magnitude axis and a phase axis;

(ii) determining a magnitude threshold and a phase threshold, said magnitude threshold and said phase threshold dividing said Cartesian plot into four zones, each of said four zones being characterized by the presence of said known cancerous tissue samples, on one hand, or said known fat and/or normal tissue samples, on the other hand; and (iii) plotting the tissue sample whose condition is unknown within said Cartesian plot whereby the location of the tissue sample within one of said four zones is indicative of whether the tissue sample is cancerous as opposed to fat or normal.

3. The method as claimed in claim 2 wherein said fluorescence spectrum is an emission spectrum.

4. The method as claimed in claim 3 wherein said illuminating step comprises illuminating the tissue sample with substantially monochromatic light at a wavelength of approximately 300 nm and wherein said obtaining step comprises measuring fluorescent light emitted from the tissue sample over a spectral band from about 320 nm to about 580 nm.

5. The method as claimed in claim 3 wherein said illuminating step comprises illuminating the tissue sample with substantially monochromatic light at a wavelength of approximately 340 nm and wherein said obtaining step comprises measuring fluorescent light emitted from the tissue sample over a spectral band from about 350 nm to about 600 nm.

6. The method as claimed in claim 3 wherein said illuminating step comprises illuminating the tissue sample with substantially monochromatic light at a wavelength of approximately 325 nm and wherein said obtaining step comprises measuring fluorescent light emitted from the tissue sample over a spectral band from about 340 nm to about 600 nm.

7. The method as claimed in claim 3 wherein said illuminating step comprises illuminating the tissue sample with substantially monochromatic light at a wavelength of approximately 310 nm and wherein said obtaining step comprises measuring fluorescent light emitted from the tissue sample over a spectral band from about 340 nm to about 600 nm.

8. The method as claimed in claim 3 wherein said illuminating step comprises illuminating the tissue sample with substantially monochromatic light at a wavelength of approximately 350 nm and wherein said obtaining step comprises measuring fluorescent light emitted from the tissue sample over a spectral band from about 360 nm to about 600 nm.

9. The method as claimed in claim 3 wherein said obtaining step comprises measuring fluorescent light emitted from the tissue sample over a spectral band from about 300 nm to about 488 nm.

10. The method as claimed in claim 2 wherein said fluorescence spectrum is a time-resolved fluorescence spectrum.

11. The method as claimed in claim 2 wherein said Fourier analysis performing step comprises determining respective magnitude and phase calculations for two non-zero order Fourier harmonics.

12. The method as claimed in claim 11 wherein said comparing step comprises comparing the respective magnitude and phase calculations for said two non-zero order Fourier harmonics.

13. The method as claimed in claim 2 wherein said Fourier analysis performing step comprises determining respective magnitude and phase calculations for three non-zero order Fourier harmonics.

14. The method as claimed in claim 13 wherein said comparing step comprises comparing the respective magnitude and phase calculations for at least two of said three non-zero order Fourier harmonics.

15. The method as claimed in claim 14 wherein said comparing step comprises comparing the respective magnitude and phase calculations for said three non-zero order Fourier harmonics.

16. The method as claimed in claim 2 wherein the tissue sample is selected from the group consisting of breast tissue, colon tissue, GYN tissue, gastrointestinal tissue, aerodigestive tissue, bladder tissue and brain tissue.

17. The method as claimed in claim 2 wherein the tissue sample is an in vitro tissue sample.

18. The method as claimed in claim 2 wherein the tissue sample is a human breast tissue sample, wherein said illuminating step comprises illuminating the human breast tissue sample with substantially monochromatic light at a wavelength of approximately 300 nm, wherein said obtaining step comprises measuring fluorescent light emitted from the human breast tissue sample over a spectral band from about 320 nm to about 580 nm and wherein said comparing step comprises comparing the magnitude and phase of one or more of the first three non-zero order Fourier transform harmonics to appropriate standards.

19. The method as claimed in claim 18 wherein said comparing step comprises determining whether both the magnitude of the first Fourier transform harmonic exceeds 0.85 and the phase of the first Fourier transform harmonic exceeds 76°, in which case the human breast tissue sample is cancerous, or does not, in which case the human breast tissue sample is not cancerous.

20. The method as claimed in claim 2 wherein the tissue sample is a human breast tissue sample and wherein said known cancerous tissue samples are situated above said magnitude threshold, said known normal tissue samples are situated below said magnitude threshold, said known cancerous tissue samples are situated above said phase threshold and said fat tissue samples are situated below said phase threshold whereby a first of said four zones is characterized by cancerous tissue samples, a second of said four zones is characterized by normal tissue samples, a third of said four zones is characterized by normal or fat tissue samples and a fourth of said four zone is characterized by fat tissue samples.

21. A method for determining if a tissue sample is cancerous or not, said method comprising the steps of:

(a) using optical spectroscopy to obtain a spectrum for the tissue sample;

(b) performing Fourier analysis on the spectrum so as to determine respective magnitude and phase calculations for a non-zero order Fourier harmonic; and (c) plotting the magnitude and phase calculations for the tissue sample on a Cartesian plot, said Cartesian plot having a magnitude axis and a phase axis, said Cartesian plot being divided into four zones by a magnitude threshold and a phase threshold, said magnitude and phase thresholds both having been determined from known cancerous and non-cancerous tissue samples, said magnitude threshold separating cancerous magnitude values on one side thereof from non-cancerous magnitude values on an opposite side thereof, said phase threshold distinguishing cancerous phase values on one side thereof from non-cancerous phase values on an opposite side thereof whereby the location of the magnitude and phase calculations for the tissue sample within one of said four zones is indicative of whether the tissue sample is cancerous or not.

22. The method as claimed in claim 21 wherein said spectrum is a Raman spectrum.

23. The method as claimed in claim 21 wherein said spectrum is an absorption spectrum.

24. The method as claimed in claim 21 wherein said spectrum is a fluorescence excitation spectrum.

25. The method as claimed in claim 24 wherein said fluorescence excitation spectrum obtaining step comprises exciting the tissue sample with light over the spectral region from about 250 nm to about 330 nm and measuring resultant fluorescence from the tissue sample at about 340 nm.

26. The method as claimed in claim 24 wherein said fluorescence excitation spectrum obtaining step comprises exciting the tissue sample with light over the spectral region from about 250 nm to about 330 nm and measuring resultant fluorescence from the tissue sample at about 380 nm.

27. The method as claimed in claim 24 wherein said fluorescence excitation spectrum obtaining step comprises exciting the tissue sample with light over the spectral region from about 250 nm to about 330 nm and measuring resultant fluorescence from the tissue sample at about 440 nm.

28. The method as claimed in claim 21 wherein said spectrum is a time-resolved spectrum.

29. The method as claimed in claim 21 wherein said spectrum is an elastic scattering spectrum.

30. The method as claimed in claim 21 wherein said known non-cancerous tissue samples include both at least one normal tissue sample and at least one fat tissue sample.

* * * * *